US008450702B2

(12) United States Patent
Hoshishima et al.

(10) Patent No.: US 8,450,702 B2
(45) Date of Patent: May 28, 2013

(54) FLUORESCENCE DETECTING METHOD AND FLUORESCENCE DETECTING DEVICE

(75) Inventors: Kazuteru Hoshishima, Okayama (JP); Hironori Hayashi, Okayama (JP); Shigeyuki Nakada, Okayama (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 368 days.

(21) Appl. No.: 12/867,448

(22) PCT Filed: Feb. 18, 2009

(86) PCT No.: PCT/JP2009/052757
§ 371 (c)(1),
(2), (4) Date: Sep. 13, 2010

(87) PCT Pub. No.: WO2009/110314
PCT Pub. Date: Sep. 11, 2009

(65) Prior Publication Data
US 2010/0320398 A1    Dec. 23, 2010

(30) Foreign Application Priority Data
Mar. 4, 2008    (JP) .................................. 2008-053057

(51) Int. Cl.
*G01N 21/64*    (2006.01)
(52) U.S. Cl.
CPC .................................. *G01N 21/6408* (2013.01)
USPC ....................................................... 250/458.1

(58) Field of Classification Search
CPC ........ G01N 2015/1402; G01N 21/6408; G01N 15/1427
USPC ....................................................... 250/458.1
See application file for complete search history.

(56) References Cited

U.S. PATENT DOCUMENTS

| 5,270,548 A | 12/1993 | Steinkamp |
| 5,317,162 A * | 5/1994 | Pinsky et al. .............. 250/461.2 |
| 2009/0012721 A1 | 1/2009 | Kimura et al. |

FOREIGN PATENT DOCUMENTS

JP    2006-226698 A    8/2006

* cited by examiner

*Primary Examiner* — Constantine Hannaher
(74) *Attorney, Agent, or Firm* — Muncy, Geissler, Olds & Lowe, PLLC (57) ABSTRACT

A fluorescence detecting method includes the steps of collecting a first fluorescence signal of the fluorescence received by a light receiving unit when the analyte passes a position irradiated with a laser beam, collecting a second fluorescence signal of the fluorescence received by the light receiving unit in the absence of the analyte at the position irradiated with the laser beam, and adjusting a first phase difference information on the first fluorescence signal with respect to the modulation signal by using a second phase difference information on the second fluorescence signal with respect to the modulation signal to obtain a third phase difference information on the fluorescence signal of the fluorescence, and obtaining a fluorescence relaxation time constant of the fluorescence based on the third phase difference information thus obtained.

6 Claims, 5 Drawing Sheets

FLUORESCENCE DETECTING METHOD AND FLUORESCENCE DETECTING DEVICE

TECHNICAL FIELD

The present invention relates to a fluorescence detecting method and a fluorescence detecting device for detecting a fluorescence emitted from an analyte by irradiating the flow of a fluid, which is a buffer solution containing the analyte such as cells and bacteria, with laser beam.

BACKGROUND ART

Flow cytometers used in medicine and biology have therein incorporated a fluorescence detecting device for identifying the kind of analyte by irradiating the analyte with laser beam and receiving the fluorescence emitted from the fluorochrome of the analyte.

Specifically, flow cytometers use a fluorescent reagent to label a suspension containing an analyte, which is a biological material such as cells, DNA, RNA, enzymes, proteins, etc., in a buffer solution and allows the analyte to flow in a sheath fluid that flows at a speed of about 10 m/s under pressure to produce a laminar sheath flow. The analyte in the flow is irradiated with laser beam, and a fluorescence emitted from the fluorochrome in the biological material is received and used as a label for identifying the biological material.

Flow cytometers can measure intracellular relative amounts of the DNA, RNA, enzymes, proteins, etc. in the cell and quickly analyze their functions. Flow cytometers also use a cell sorter or the like for identifying specific types of cells and chromosomes using a fluorescence to quickly sort and collect only the identified cells and chromosomes alive.

Flow cytometers are required to quickly identify more analytes from fluorescence information in such applications.

Patent Document 1 below describes a fluorescence detecting device. That fluorescence detecting device time-modulates the intensity of laser beam emitted from a laser light source unit and irradiates a biological material, etc. with that laser beam. The fluorescence emitted from the sample is received, and its phase difference information with respect to the modulation signal for the laser beam is used to calculate the fluorescence relaxation time constant of the fluorescence emitted from the biological material, and the like. This supposedly permits identification of many kinds of fluorescences, especially quick and efficient identification of fluorescence signals.

CITATION LIST

[Patent Document]
[Patent document 1] JP 2006-226698 A

DISCLOSURE OF THE INVENTION

Problems to be Solved by the Invention

A problem encountered with the device described in the Patent Document 1 is that it may accurately identify the kind of received fluorescence when the fluorescence intensity of the fluorescence emitted from a biological material, etc. is strong, but is not necessarily capable of accurate identification when the emission region of the fluorescence emitted from the biological material, etc. is limited and the fluorescence intensity is relatively weak.

Where, for example, the fluorescence emitted from a fluorochrome having a known fluorescence relaxation time constant has been previously measured and the fluorescence intensity is weak, there arises a difference between the obtained fluorescence relaxation time constant and the known fluorescence relaxation time constant, making an accurate identification impossible. Another problem is that in a histogram where a plurality of fluorescence relaxation time constants, each obtained each time a biological material passes a point irradiated with laser beam, are plotted on the horizontal axis against the frequency on the vertical axis, the mountain forming the histogram exhibits a broad shape and thus an accurate identification of a plurality of fluorescences is impossible.

Today there are an increasing number of cases dealing with a biological material having a fluorescence emission region limited to an extremely small, localized region thereof. In such cases, the fluorescence intensity is necessarily weak because of the small fluorescence emission region from which a biological material emits fluorescence. This makes accurate fluorescence identification still more difficult as described above.

It is therefore an object of the present invention to provide a fluorescence detecting method and a fluorescence detecting device capable of more accurate calculation of the fluorescence relaxation time constant than is conventionally possible when detecting the fluorescence emitted from an analyte such as a biological material by laser beam irradiation to overcome the above problems.

Means to Solve the Problems

In order to achieve the object, the present invention provide a fluorescence detecting method of detecting a fluorescence emitted from an analyte by irradiating a flowing fluid formed of a buffer solution containing the analyte with laser beam having its light intensity modulated using a modulation signal having a given frequency and receiving the fluorescence emitted from a passing analyte with a light receiving means, the method comprising:

a first step of collecting a first fluorescence signal of the fluorescence received by the light receiving means when the analyte passes a position irradiated with the laser beam;

a second step of collecting a second fluorescence signal of the fluorescence received by the light receiving means in the absence of the analyte at the position irradiated with the laser beam after the analyte passed the position irradiated with the laser beam; and a third step of adjusting a first phase difference information on the first fluorescence signal with respect to the modulation signal by using a second phase difference information on the second fluorescence signal with respect to the modulation signal to obtain a third phase difference information on the fluorescence signal of the fluorescence emitted from the analyte with respect to the modulation signal, and obtaining a fluorescence relaxation time constant of the fluorescence emitted from the analyte based on the third phase difference information thus obtained.

Preferably, each of the first and the second phase difference information is data comprising a value of a signal component that is in phase with the modulation signal and a value of a signal component that is 90 degrees out of phase with the modulation signal. Further, it is preferable that the third phase difference information is data obtained by subtracting the second phase difference information from the first phase difference information by component.

Also, the present invention provide a fluorescence detecting device for detecting a fluorescence emitted from an analyte by irradiating a flowing fluid formed of a buffer solution containing the analyte with laser beam, the device comprising:

a laser light source unit for emitting toward the flow laser beam having its light intensity modulated using a modulation signal having a given frequency;

a light receiving unit for generating a fluorescence signal of a fluorescence emitted by laser beam irradiation;

a timing detector for detecting a timing at which the analyte passes a position irradiated with the laser beam; and a processing/analyzing means for collecting a first fluorescence signal of a fluorescence received by the light receiving unit at a detected timing, collecting a second fluorescence signal of the fluorescence received by the light receiving unit in the absence of the analyte at a position irradiated with the laser beam after the analyte passed a position irradiated with the laser beam, adjusting a first phase difference information on the first fluorescence signal with respect to the modulation signal by using a second phase difference information on the second fluorescence signal with respect to the modulation signal to obtain a third phase difference information on the fluorescence signal of the fluorescence emitted from the analyte, and obtaining a fluorescence relaxation time constant of the fluorescence emitted from the analyte based on the third phase difference information thus obtained.

Preferably, each of the first and the second phase difference information is data comprising a value of a signal component that is in phase with the modulation signal and a value of a signal component that is 90 degrees out of phase with the modulation signal. Further, it is preferable that the processing/analyzing means obtains the third phase difference information by subtracting the second phase difference information from the first phase difference information by component.

Advantageous Effects of the Invention

The fluorescence detecting method and the fluorescence detecting device of the invention measure not only the fluorescence emitted from the analyte but the fluorescence emitted from the buffer solution after the analyte has passed the position irradiated with laser beam. The reason for this is that when the fluorescence emitted from the analyte is relatively weak, the fluorescence emitted from the buffer solution cannot be neglected. The fluorescence measured as the analyte passes the position irradiated with laser beam contains fluorescence emitted from the buffer solution besides fluorescence emitted from the analyte. According to the invention, since the fluorescence emitted from the buffer solution after the analyte has passed the position irradiated with laser beam is also measured, phase difference information on the fluorescence emitted from the analyte can be accurately obtained using the measurements thus obtained. Thus, calculation of the fluorescence relaxation time constant can be achieved more accurately and quickly than is conventionally possible.

DESCRIPTION OF EMBODIMENTS

Now the invention will be described in detail below based on a flow cytometer suitably using the fluorescence detecting device of the invention implementing the fluorescence detecting method of the invention.

Figure 1:
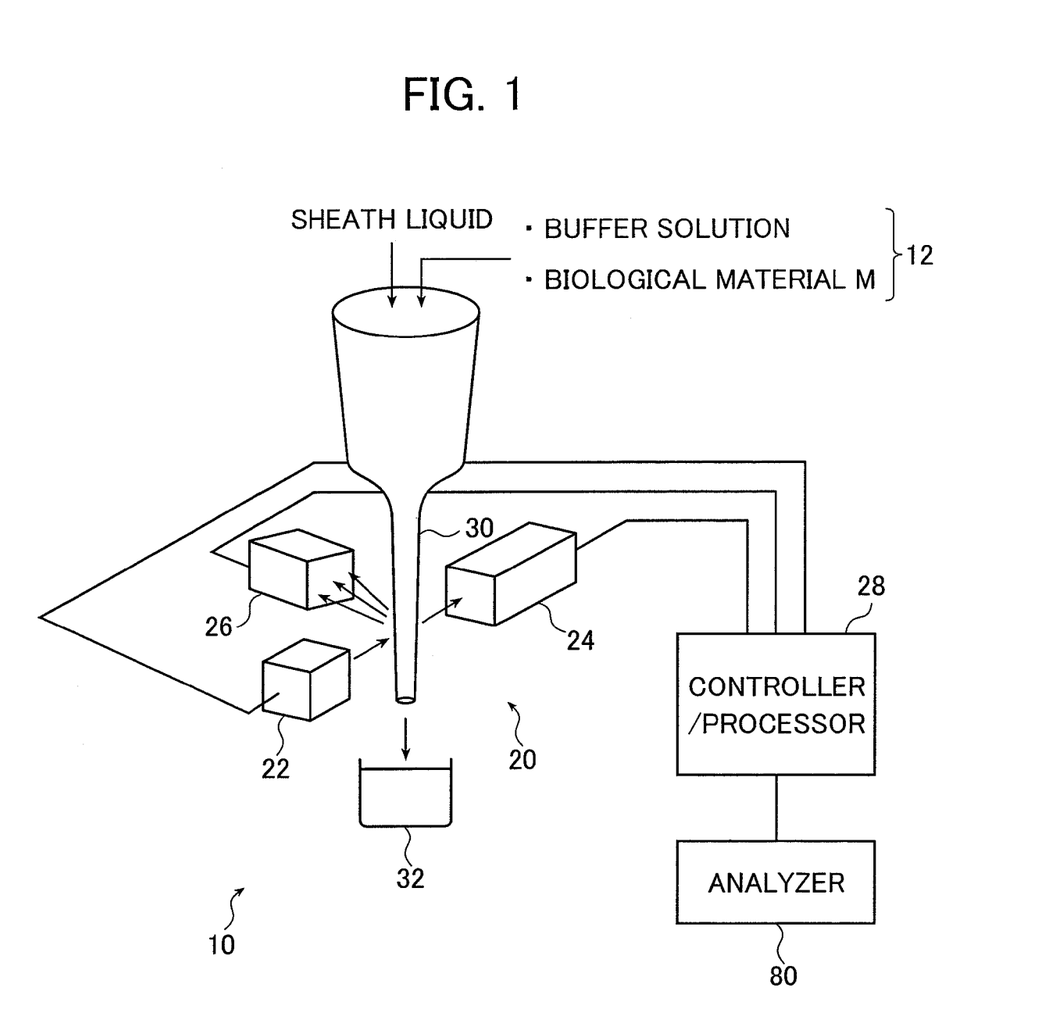
FIG. 1 is a schematic view illustrating a configuration of a flow cytometer using the fluorescence detecting device of the invention.

FIG. 1 is a schematic view illustrating a flow cytometer 10 using a fluorescence detecting device employing intensity-modulated laser beam. Although it is a biological material M having a fluorochrome suspended in a buffer solution that is measured in the following description of an embodiment, both the biological material M and microbeads contained in a buffer solution may be the analyte to be measured, provided that the microbeads have a given fluorochrome and biologically bind to the biological material M.

The flow cytometer 10 comprises a signal processor 20 and an analyzer (computer) 80, wherein the processor 20 emits laser beam to irradiate a sample 12 that is prepared by suspending the biological material M, which fluoresces by laser beam irradiation, in a buffer solution in order to detect and process a fluorescence signal of the fluorescence generated by a fluorochrome possessed by the biological material M in the sample 12 while the analyzer 80 (computer) analyzes an analyte in the sample 12 from the processing results yielded by the signal processor 20.

The signal processor 20 comprises a laser light source 22, light receiving units 24, 26, a controller/processor 28 including a controller for providing control to generate a modulation signal for intensity-modulating laser beam emitted by the laser light source unit 22 with a given modulation frequency and a signal processor for identifying a fluorescence signal given by the sample 12, a duct 30 for allowing the sample 12 composed of a buffer solution containing the biological material M to flow in a high-speed sheath liquid to form a laminar sheath flow.

Disposed near the outlet of the duct 30 is a collector 32. The flow cytometer 10 may comprise a cell sorter for identifying the biological material M in the sample 12 by laser beam irradiation to sort the biological M into separate collectors within a short time period The laser light source unit 22 emits three laser beams having different wavelengths: e.g. $\lambda_1$=405 nm, $\lambda_2$=533 nm, and $\lambda_3$=650 nm. A lens system is provided to cause the laser beam to focus at a given position in the duct 30 so that a measuring point for measuring the sample 12 is formed at the focusing position. The measuring point corresponds to the position that is irradiated with laser beam according to the invention.

Figure 2:
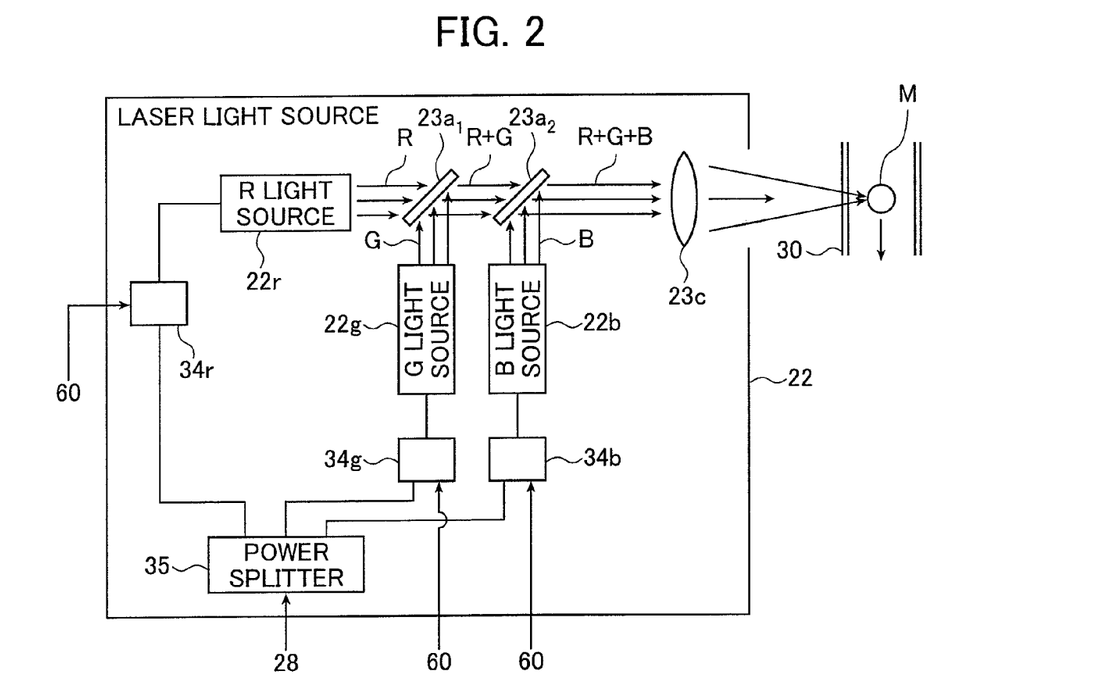
FIG. 2 is a schematic view illustrating a configuration of an example of a laser light source used in the fluorescence detecting device of the invention.

FIG. 2 is a view illustrating an example of configuration of the laser light source unit 22.

The laser light source unit 22 emits intensity-modulated laser beam having a wavelength in a visible light bandwidth of 350 to 800 nm.

The laser light source unit 22 comprises an R light source 22r that emits red laser beam R as CW (continuous wave) laser beam and modulates the intensity of the CW laser beam with a given frequency; a G light source 22g that emits green laser beam G as CW (continuous wave) laser beam and modulates the intensity of this CW laser beam with a given frequency; and a B light source 22b that emits blue laser beam B as CW (continuous wave) laser beam and modulates the intensity of this CW laser beam with a given frequency.

The laser light source unit 22 further comprises dichroic mirrors $23a_1$, $23a_2$ that passes laser beam having a given frequency band, reflecting laser beam having the other frequency bands; a lens system 23c for causing laser beam composed of the laser beams R, G, and B to focus at the measuring point in the duct 30; laser drivers 34r, 34g, and 34b for driving the R light source 22r, the G light source 22g, and the B light source 22b, respectively; and a power splitter 35 for distributing a supplied signal to the laser drivers 34r, 34g, and 34b.

Semiconductor lasers, for example, are used as the laser light sources for emitting these laser beams.

Each laser beam has a power of about 5 mW to 100 mW. The frequency for modulating the intensity of the laser beam (modulation frequency), on the other hand, is 10 to 50 MHz in which a cycle is slightly longer than the fluorescence relaxation time constant.

The dichroic mirror $23a_1$ passes the laser beam R and reflects the laser beam G; the dichroic mirror $23a_2$ passes the laser beams R and G and reflects the laser beam B.

The above configuration combines the laser beams R, G, and B to produce irradiation light for irradiating the sample 12 located at the measuring point.

Each of the R light source 22r, the G light source 22g, and the B light source 22b oscillates in a given wavelength band so that the laser beams R, G, and B excite the fluorochrome to produce fluorescence having a specific wavelength band. The fluorochrome excited by the laser beams R, G, and B are attached to the biological material M to be measured, and the biological material M produces fluorescence with a specific wavelength as it is irradiated with the laser beams R, G, and B at the measuring point when passing through the duct 30 as an object to be measured. Irradiation of the buffer solution with the laser beam is continued for a given time period in the absence of the biological material M after, and preferably immediately after, the biological material M passed the measuring point, to detect the fluorescence produced by the buffer solution.

The light receiving unit 24 is disposed opposite the laser light source unit 22 with the duct 30 between them and comprises a photoelectric converter that generates a detection signal indicating the passage of the biological material M by the measuring point in response to the forward scattering of the laser beam as the biological material M passes the measuring point. The signal generated by the light receiving unit 24 is supplied to the control/processor 28 to be used therein as a trigger signal for indicating the timing at which the biological material M passes the measuring point in the duct 30.

A time T it takes the biological material M to pass the measuring point is expressed by T=(D+W)/V, where D is a mean diameter of the biological material M, V the speed at which the biological material M flows through the flow cell, and W the spot width of the laser beam at the measuring point. The time T is a known value. The signal processor 20 starts detecting the fluorescence using the trigger signal generated by the light receiving unit 24 as a timing for starting measurement and continues measurement for a period of 2T, a period that is double the time T. Measurement herein means receiving the fluorescence generated by the sample 12 during the time T, performing signal processing at the control/processor 28 described later, and supplying phase difference information to the analyzer 80. This measurement achieves acquisition of a first fluorescence signal of the fluorescence received by the light receiving unit 26 as the biological material M passes the measuring point and a second fluorescence signal of the fluorescence received by the light receiving unit 26 after the biological material M passed the measuring point in the absence of the biological material M, hence only in the presence of the buffer solution.

The light receiving unit 26 is disposed normal to the direction in which the laser beam is emitted from the laser light source unit 22 and normal to the direction in which the sample 12 moves in the duct 30. The light receiving unit 26 comprises a photoelectric converter for receiving fluorescence emitted from the sample 12 irradiated at the measuring point.

Figure 3:
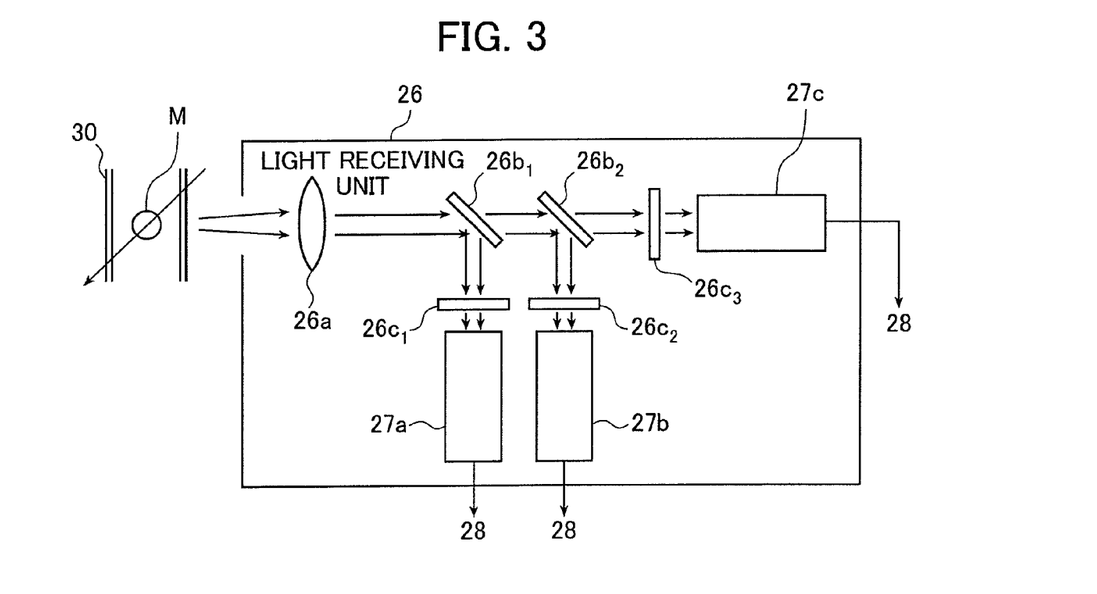
FIG. 3 is a schematic view illustrating a configuration of an example of a light receiving unit used in the fluorescence detecting device of the invention.

FIG. 3 is a schematic view illustrating a configuration of an example of the light receiving unit 26.

The light receiving unit 26 illustrated in FIG. 3 comprises a lens system 26a for focusing the fluorescence signal emitted from the biological material M in the sample 12, dichroic mirrors $26b_1$, $26b_2$, band pass filters $26c_1$ to $26c_3$, and photoelectric converters 27a to 27c such as photomultipliers.

The lens system 26a is configured so that the fluorescence admitted in the light receiving unit 26 focuses on the light receiving surfaces of the photoelectric converters 27a to 27c.

Each of the dichroic mirrors $26b_1$, $26b_2$ reflects a fluorescence having a given range of wavelength band, passing the other fluorescences. The reflecting wavelength bands and passing wavelength bands in the dichroic mirrors $26b_1$, $26b_2$ are set so that the photoelectric converters 27a to 27c may receive given wavelength bands of fluorescence after filtering through the band pass filters $26c_1$ to $26c_3$.

The band pass filters $26c_1$ to $26c_3$ are provided in front of the light receiving surfaces of the photoelectric converters 27a to 27c to pass only the fluorescence having given wavelength bands, respectively. The given wavelength bands are determined according to the wavelength band of the fluorescence generated by the fluorochrome.

The photoelectric converters 27a to 27c, each comprising a sensor provided, for example, with a photomultiplier, are sensors that convert light received at the photoelectric surface into an electric signal. The fluorescences are received as optical signals having phase difference information with respect to the modulation signal for the laser beam. Thus, the generated electric signals are fluorescence signals having phase difference information. The fluorescence signals are amplified by the amplifiers and supplied to the controller/processor 28.

Figure 4:
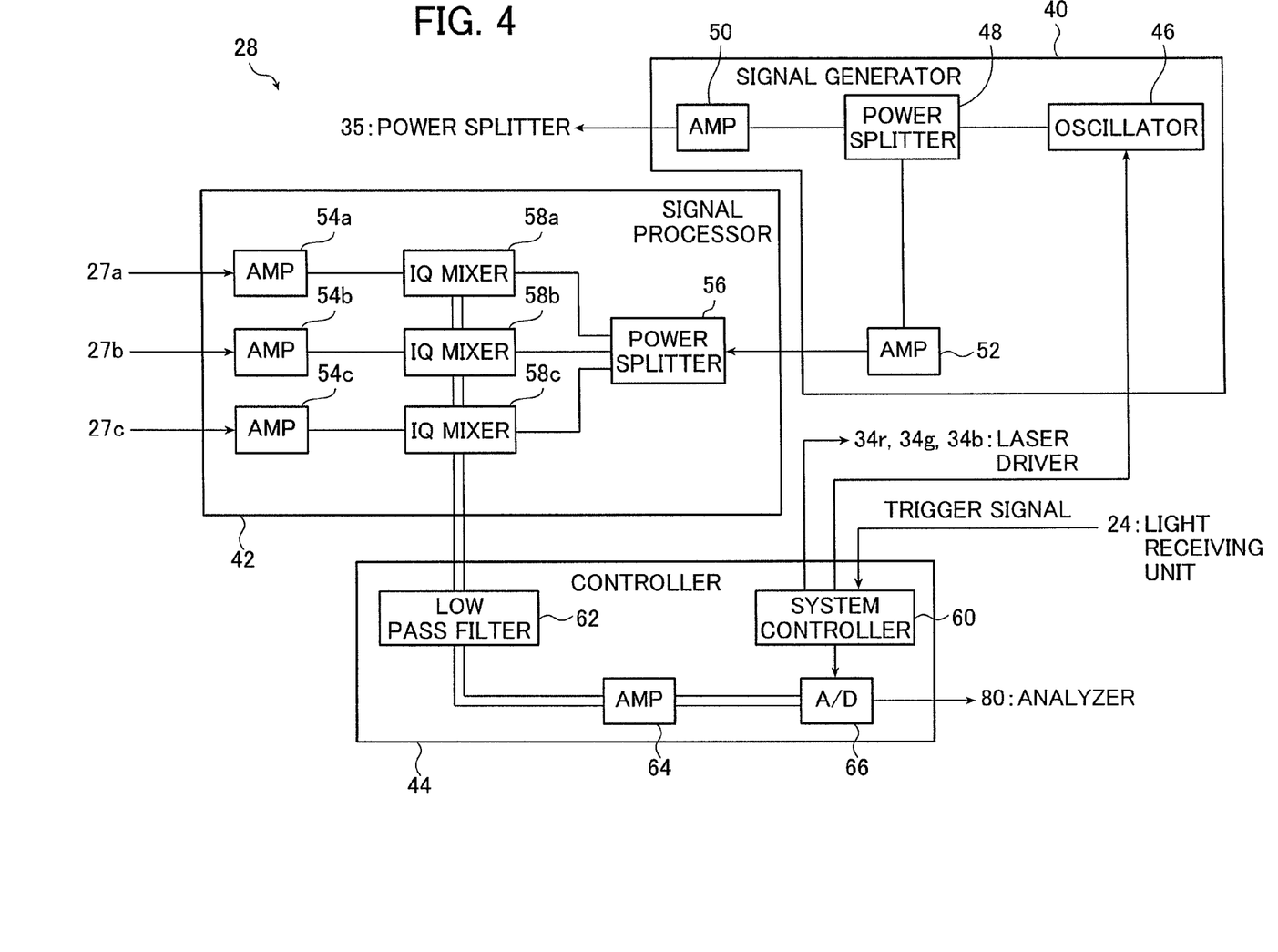
FIG. 4 is a schematic view illustrating a configuration of an example of a controller/processor used in the fluorescence detecting device of the invention.

As illustrated in FIG. 4, the controller/processor 28 comprises a signal generator 40, a signal processor 42, and a controller 44. The signal generator 40 and the controller 44 constitute a light source controller for generating a modulation signal having a given frequency. The controller/processor 28 corresponds to a portion for acquiring the first fluorescence signal and the second fluorescence signal according to the invention.

The signal generator 40 generates a modulation signal for modulating the intensity of the laser beam (amplitude modulation) with a given frequency.

Specifically, the signal generator 40 comprises an oscillator 46, a power splitter 48, and amplifiers 50, 52, and supplies the generated modulation signal to the power splitter 35 of the laser light source unit 22 and also to the signal processor 42. The modulation signal supplied to the signal processor 42 is used as a reference signal for detecting the fluorescence signals (the first fluorescence signal and the second fluorescence signal) outputted from the photoelectric converters 27a to 27c as will be described. The modulation signal is a sine wave signal having a given frequency and set to a frequency range of 10 MHz to 50 MHz.

The signal processor 42 uses the fluorescence signals outputted from the photoelectric converters 27a to 27c to process signals containing phase difference information on the fluorescence emitted from the sample 12 by laser beam irradiation. The signal processor 42 comprises amplifiers 54a to 54c for amplifying the fluorescence signals outputted from the photoelectric converters 27a to 27c, a power splitter 56 for distributing the modulation signal, which is a sine wave signal supplied from the signal generator 40, to each of the amplified fluorescence signals, and IQ mixers 58a to 58c for combining the amplified fluorescence signals using the modulation signal as reference signal.

Figure 5:
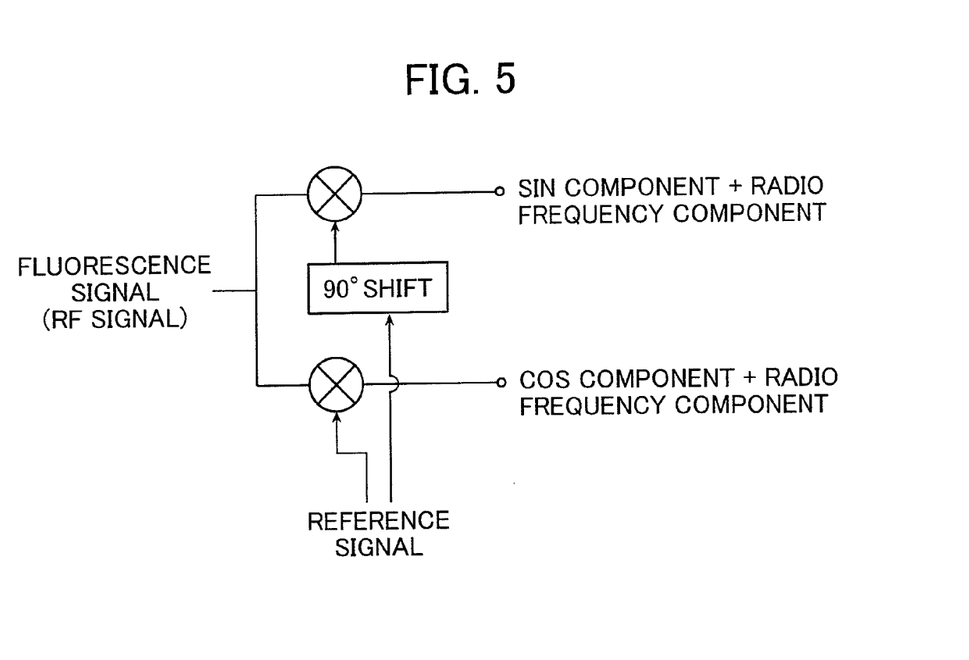
FIG. 5 is a view for explaining an IQ mixer used in the controller/processor illustrated in FIG. 4.

The IQ mixers 58a to 58c combine the fluorescence signals supplied from the photoelectric converters 27a to 27c by using the modulation signal supplied from the signal generator 40 as a reference signal. Specifically, as illustrated in FIG. 5, each of the IQ mixers 58a to 58c multiplies the fluorescence signal (RF signal) by the reference signal to calculate a processing signal containing the cosine component (a signal component in phase with the reference signal) and a radio frequency component of the fluorescence signal and multiplies the fluorescence signal by a signal that is 90 degrees out of phase with the reference signal to calculate another processing signal containing the sine component (a signal component 90 degrees out of phase with the reference signal) and a radio frequency component of the fluorescence signal. These processing signals containing the cosine component and the sine component are supplied to the controller 44.

The controller 44 provides control such that the signal generator 40 produces a modulation signal (sine wave signal) having a given frequency and, in addition, removes a radio frequency component from the processing signals containing the cosine component and the sine component of the fluorescence signal obtained by the signal processor 42 in order to obtain the value of the cosine component and the value of the sine component of the fluorescence signal.

Specifically, the controller 44 comprises a system controller 60 for giving instructions to control the operations of the relevant components of the signal processor 20 and controlling all the operations performed by the flow cytometer 10; a low pass filter 62 for removing a radio frequency component from the processing signals having the radio frequency component added to the cosine component and the sine component calculated by the signal processor 42; an amplifier 64 for amplifying the processing signals containing the cosine component and the sine component and having the radio frequency component removed; and an analog-to-digital converter 66 for sampling the amplified processing signals.

The system controller 60 determines the oscillation frequency of the oscillator 46 for intensity modulation of the laser beam.

The controller 44 uses the amplifier 64 to amplify the value of the cosine component and the value of the sine component from which the radio frequency signal has been removed through filtering by the low pass filter 62 and uses the analog-to-digital converter 66 to sample the amplified values and supply the digitized processing signals of the cosine component and the sine component to the analyzer 80.

The analyzer 80 obtains the fluorescence relaxation time constant (fluorescence relaxation time) of the fluorescence emitted from the biological material M and uses the fluorescence relaxation time constant to identify the kind of the fluorescence of the biological material M in the sample 12. The sample 12 may be added with microbeads having a given fluorochrome attached thereto to examine the properties of the biological material M such as its possibility of biological binding.

The analyzer 80 constitutes a processor for calculating the fluorescence relaxation time constant according to the invention and may be configured by a computer.

The calculation of the fluorescence relaxation time constant of the fluorescence emitted from the biological material M uses phase difference information on the first fluorescence signal of the fluorescence emitted from the biological material M suspended in the buffer solution as the biological M passes the measuring point with respect to the modulation signal and phase difference information on the second fluorescence signal of the fluorescence emitted from the buffer solution immediately after the biological material M passed the measuring point with respect to the modulation signal.

As described above, measuring is started in response to the trigger signal produced by the light receiving unit 24 and continued for a period of 2T, double the time T it takes the biological material M to pass the measuring point. Thus, in a time period from the start of the measurement to a first point in time T, detected is the fluorescence emitted as the biological material M suspended in the buffer solution passes the measuring point, and in a time period from the point in time T to 2T, detected is the fluorescence emitted from the buffer solution immediately after the biological material M passed the measuring point. Thus, the processing signals including the cosine component and the sine component supplied to the analyzer 80 contains the phase difference information of the fluorescence from the start of the measurement to the time T, i.e., the phase difference information of the fluorescence emitted from the buffer solution and the biological material M, and the phase difference information of the fluorescence from the time T to the time 2T, i.e., the phase difference information of the fluorescence emitted from the buffer solution.

Figure 6:
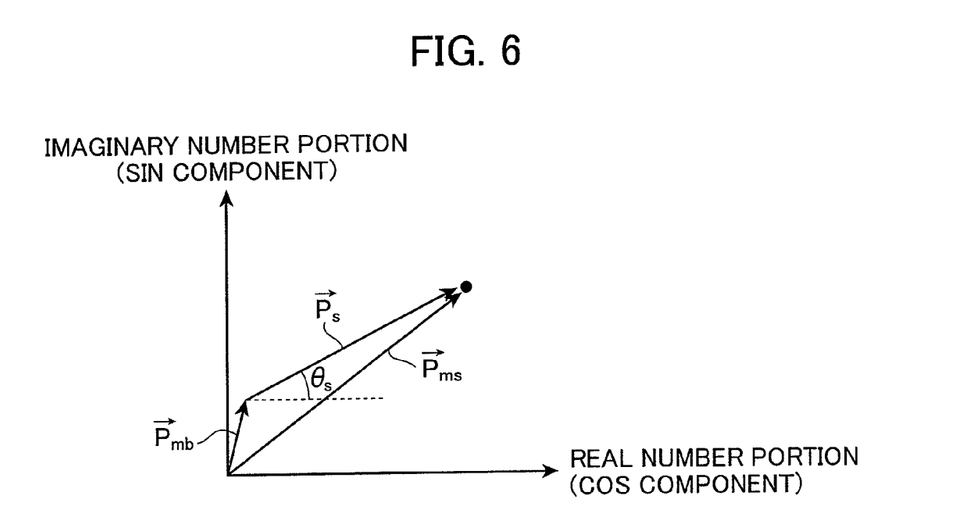
FIG. 6 is a view for explaining the calculation of a fluorescence relaxation time constant performed in the fluorescence detecting device of the invention.

To be specific, the calculation of the fluorescence relaxation time constant of the fluorescence emitted from the biological material M uses measuring vectors, which contain as vector components the above described cosine component and the sine component supplied from the controller 44, as data containing phase difference information. These measuring vectors have a relationship expressed by Ps=Pms−Pmb, where Pms is the measuring vector of the first fluorescence signal emitted as the biological material M suspended in the buffer solution passes the measuring point, Pmb is the measuring vector of the second fluorescence signal emitted from the buffer solution immediately after the biological material M passed the measuring point, and Ps is the vector of the biological material M composed of the cosine component and the sine component of the fluorescence emitted from the biological material M. FIG. 6 illustrates the relationship between the measuring vectors Pms, Pmb, and the vector Ps of the biological material M. The graph illustrated in FIG. 6 plots the value (amplitude) of the cosine component (real number portion) of the modulation signal of the laser beam on the horizontal axis against the value (amplitude) of the sine component (imaginary number portion) on the vertical axis. Thus, the phase difference information in the present invention is data composed of the value of a signal component (cosine component) that is in phase with the modulation signal and the value of a signal component (sine component) that is 90 degrees out of phase with the modulation signal.

Figure 7:
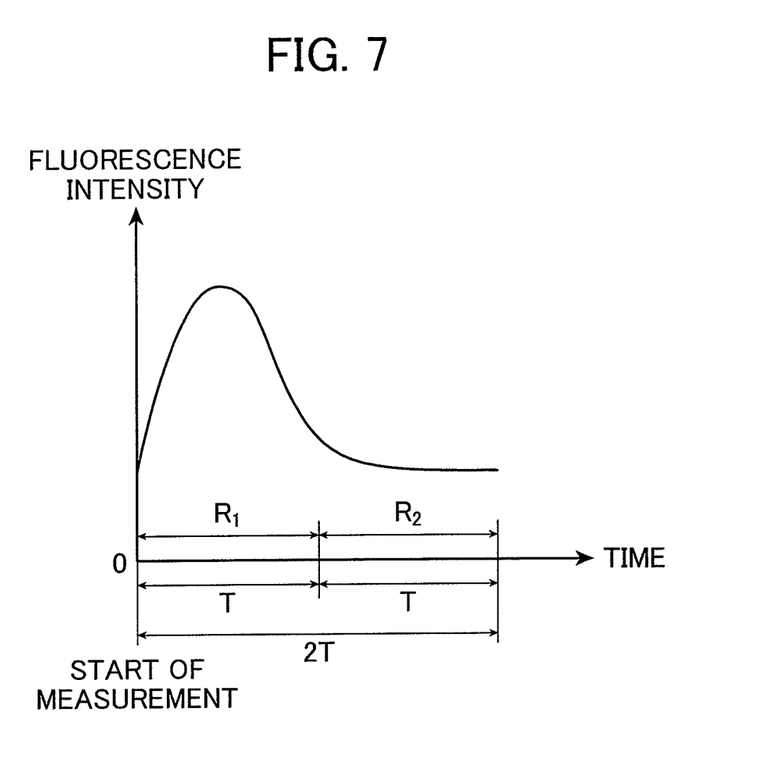
FIG. 7 is a view illustrating how the fluorescence intensity changes with time.

Actually, the fluorescence emitted from the sample 12 as the biological material M passes the measuring point contains fluorescence emitted from the biological material M and fluorescence emitted from the buffer solution. Therefore, the light receiving unit 26 receives the fluorescence where these fluorescences are mixed. Accordingly, the measuring vector Pms obtained by the analyzer 80 contains the value of the cosine component and the value of the sine component of the fluorescence signal of the fluorescence emitted from the biological material M and the value of the cosine component and the value of the sine component of the fluorescence signal of the fluorescence emitted from the buffer solution. Therefore, the vector Ps of the fluorescence emitted from the biological material M can be calculated by subtracting from the measuring vector Pms the vector Pmb composed of the value of the cosine component and the value of the sine component of the fluorescence signal of the fluorescence emitted from the buffer solution immediately after the biological material M passed the measuring point. In other words, the vector Ps of the fluorescence emitted from the biological material M is calculated by subtracting, by component, the value of the cosine component and the value of the sine component of the measuring vector Pmb from the value of the cosine component and the value of the sine component of the measuring vector Pms.

Where the fluorescence of the biological material M is weak, the fluorescence emitted from the buffer solution and contained in the fluorescence signal of the fluorescence of the biological material M as a background component cannot be neglected. In this embodiment, the vector Ps of the fluorescence emitted from the biological material M is calculated by, as described above, measuring the fluorescence emitted from the buffer solution for a certain time period immediately after the biological material M passed the measuring point (for a time period from the point in time T to 2T), for example, for the same length of time as the time T it takes the biological material M to pass the measuring point. FIG. 7 illustrates how the fluorescence intensity of the fluorescence emitted from the sample 12 changes with time. A region R1 in the graph of FIG. 7 is a region where the fluorescence emitted from the biological material M and the fluorescence emitted from the buffer solution both exist. A region R2 is a region where only the fluorescence emitted from the buffer solution exists. Thus, the measurement in the region R1 is started upon generation of the trigger signal outputted from the light receiving unit 24 as a timing for starting the measurement and continued for a period of time T from the start of measurement, the immediately followed by measurement in the region R2. The calculation of the vector Ps is performed for every fluorescence signal obtained by the photoelectric converters 27a to 27c.

The analyzer 80 calculates the fluorescence relaxation time constant (fluorescence relaxation time) from the thus obtained vector Ps of the fluorescence emitted from the biological material M. The fluorescence relaxation time constant is calculated using the measuring vectors Pms and Pmb supplied each time the biological material M passes the measuring point. Therefore, the analyzer 80 produces a histogram showing the frequency of the calculated fluorescence relaxation time constant and statistically processes the fluorescence relaxation time constant to obtain a mean fluorescence relaxation time constant and its dispersion. Thus, the fluorescence emitted from the biological material M can be identified.

The method of calculating the fluorescence relaxation time constant depends on the fluorescence relaxation time constant of the fluorescence emitted from the fluorochrome. When the fluorescence is expressed by a first order relaxation process, for example, the fluorescence relaxation time constant is calculated according to the following formula.

$$\tau = 1/\Omega \cdot \tan \theta_s$$

In the formula, $\theta_s$ is the tilt angle of the calculated vector Ps with respect to the axis corresponding to its cosine component axis (see FIG. 6), $\omega$ is the frequency of the modulation signal for the laser beam, and $\tau$ is the fluorescence relaxation time constant. The fluorescence relaxation time constant $\tau$ denotes a time from a point in time when the laser beam is pulse-irradiated until a point in time when a fluorescence intensity becomes $I_0/e$ (e is a base of natural logarithm, $e \approx 2.71828$), where $I_0$ is the initial fluorescence intensity when the laser beam is pulse-irradiated.

This is how the flow cytometer 10 is configured.

The signal processor 20 of the flow cytometer 10 as described above causes the oscillator 46 to generate a modulation signal having a given frequency in response to the instruction from the controller 44, the signal being amplified by the amplifier 50 and supplied to the laser light source unit 22 and the signal processor 42.

In this state, sample 12 flows through the duct 30 to form a flow. The flow has a flow rate of, for example, 1 m/s to 10 m/s with a flow diameter of 100 μm.

When the biological material M passing the measuring point is irradiated with the laser beam, a detection signal detecting the passage of the biological material M is outputted as a trigger signal from the light receiving unit 24 to the controller 44.

The controller 44 uses the detection signal as a trigger signal to supply a measurement start instruction signal to relevant components.

The laser beam emitted from the laser light source unit 22 is used to excite the fluorochrome in the sample 12 at the measuring point. The irradiation with the laser beam causes the fluorochrome to emit fluorescence, which is received by the light receiving unit 26. Since the laser beam is modulated in intensity with a given frequency, the fluorescence is also modulated in intensity with a given frequency accordingly.

The fluorescence emitted from the fluorochrome when irradiated with laser beam has information on phase difference with respect to the modulation signal that modulates the intensity of the laser beam.

In a time period of several microseconds to several tens of microseconds in which the biological material M passes the measuring point, the biological material M is irradiated with laser beam that is modulated in amplitude with a given frequency. The modulation frequency of the laser beam is 10 MHz to 50 MHz, for example.

In the time period of T from the start of the measurement in which the biological material M passes the measuring point, measurement of the fluorescence, i.e., the measurement in the region R1 illustrated in FIG. 7, is performed to obtain the first fluorescence signal, and in another time period of T immediately following the elapse of the time T, another measurement of the fluorescence, i.e., the measurement in the region R2 illustrated in FIG. 7, is performed to obtain the second fluorescence signal The first and the second fluorescence signals received and outputted by the photoelectric converters 27a to 27c of the light receiving unit 26 are amplified by the amplifiers 54a to 54c and combined with the modulation signals, sine wave signals, supplied from the signal generator 40 by the IQ mixers 58a to 58c.

Each of the IQ mixers 58a to 58c produces synthesized signals obtained by multiplying the modulation signal (reference signal), a sine wave signal, by the first and the second fluorescence signals and also produces synthesized signals obtained by multiplying a signal that is 90 degrees out of phase with the modulation signal (reference signal), a sine wave signal, by the first and the second fluorescence signals.

Then, the two synthesized signals generated with the first fluorescence signal are supplied to the low pass filter 62 of the controller 44 for removal of the radio frequency component to obtain the cosine component and the sine component of the first fluorescence signal. The signals of the cosine component and the sine component of the first fluorescence signal are amplified, undergo analog-to-digital conversion, and are supplied to the analyzer 80. The analog-to-digital conversion performs sampling as it is synchronized at the timing of the trigger signal supplied from the light receiving unit 24 and the sampling is done.

Similarly, the two synthesized signals generated with respect to the second fluorescence signal are supplied to the low pass filter 62 of the controller 44 for removal of the radio frequency component to obtain the cosine component and the sine component of the second fluorescence signal. The signals of the cosine component and the sine component of the second fluorescence signal are amplified, undergo analog-to-digital conversion, and are supplied to the analyzer 80.

Such signal processing is performed on time when the first and the second fluorescence signals obtained by measurement are supplied from the photoelectric converters 27a to 27c so that the value of the cosine component and the value of the sine component after signal processing are sequentially supplied to the analyzer 80.

After sequentially collecting the supplied values of the cosine component and the sine component, the analyzer 80 obtains the difference between a mean measuring vector Pms in the region R1 and a mean measuring vector Pmb in the region R2 calculated using the value of the cosine component and the value of the sine component to find the vector Ps of the biological material M. Further, the analyzer 80 uses the vector Ps to obtain the fluorescence relaxation time constant according to the formula $\tau=1/\Omega \cdot \tan \theta_s$.

Thus, according to this embodiment, the fluorescence emitted from the buffer solution is also measured immediately after the fluorescence emitted from the biological material M is measured as it passes the measuring point to calculate a fluorescence relaxation time constant using information on these measurements. Thus, the fluorescence relaxation time constant of the fluorescence emitted from the biological material M can be calculated accurately and efficiently.

The fluorescence relaxation time constant of the fluorescence emitted from the biological material M may be calculated by an alternative method whereby, without measuring the fluorescence emitted from the buffer solution each time the biological material M passes the measuring point, the fluorescence relaxation time constant of the fluorescence emitted from the buffer solution is previously measured and stored in the analyzer 80 so that the fluorescence relaxation time constant of the fluorescence emitted from the biological material M may be calculated based on the measurements obtained by measuring the fluorescence as the biological material M passes the measuring point and the fluorescence relaxation time constant of the fluorescence emitted from the buffer solution stored in the analyzer 80.

In the above method, however, measurement cannot be quickly performed when there are a plurality of samples 12 in great amounts that need to be all measured within a given time period and there are a plurality of kinds of buffer solutions. Further, where the sample 12 is prepared by diluting a culture medium containing cells, etc. having fluorescence protein introduced thereinto, the amount of the culture medium contained in the sample 12 may change depending upon the degree of dilution, and the fluorescence relaxation time constant of the fluorescence emitted from the buffer solution also changes, which cannot be handled by the above method.

Further, the composition of the buffer solution changes due to the biological activities of the biological material M, and the fluorescence relaxation time constant of the fluorescence emitted from the buffer solution also changes, which cannot be handled by the above method.

This embodiment solves the above disadvantages and permits quick and accurate calculation of the fluorescence relaxation time constant.

Instead of by using the processing method by the signal processor 42 and the controller 44 described above in this embodiment, the measuring vectors Pms and Pmb may also be obtained by using a frequency analyzer to obtain the frequency spectrum of a transfer function where the input signal is the modulation signal for the laser beam and the response signal is the processing signals outputted from the IQ mixers 58a to 58c, and obtaining the value of the real number portion and the value of the imaginary number portion in this frequency spectrum to use the value of the real number portion and the value of the imaginary number portion of the DC component as vector components of the measuring vectors Pms and Pm so that the vector Ps=Pms−Pmb of the fluorescence emitted from the biological material M may be obtained, which permits calculation of the fluorescence relaxation time constant.

While the fluorescence detecting device and the fluorescence detecting method of the invention have been described above in detail with reference to a specific embodiment, it is to be understood that various changes and modifications may be made without departing from the spirit of the invention.

[Reference Signs List]
10 flow cytometer
12 sample
20 signal processor
22 laser light source unit
22r R light source
22g G light source
22b B light source
23$a_1$, 23$a_2$, 26$b_1$, 26$b_2$ dichroic mirrors
23c, 26a lens system
24, 26 light receiving unit
26$c_1$, 26$c_2$, 26$c_3$ band pass filters
27a to 27c photoelectric sensors
28 controller/processor
30 duct
32 collector
34r, 34g, 34b laser drivers
35, 48, 56 power splitter
40 signal generator
42 signal processor
44 controller
46 oscillator
50, 52, 54a, 54b, 54c, 64 amplifiers
58a, 58b, 58c IQ mixers
62 low pass filter
66 analog-to-digital converter
80 analyzer

The invention claimed is:

1. A fluorescence detecting method of detecting a fluorescence emitted from an analyte by irradiating a flowing fluid formed of a buffer solution containing the analyte with laser beam having its light intensity modulated using a modulation signal having a given frequency and receiving the fluorescence emitted from a passing analyte with a light receiving means, the method comprising:

a first step of collecting a first fluorescence signal of the fluorescence received by the light receiving means when the analyte passes a position irradiated with the laser beam;

a second step of collecting a second fluorescence signal of the fluorescence received by the light receiving means in the absence of the analyte at the position irradiated with the laser beam after the analyte passed the position irradiated with the laser beam; and a third step of adjusting a first phase difference information on the first fluorescence signal with respect to the modulation signal by using a second phase difference information on the second fluorescence signal with respect to the modulation signal to obtain a third phase difference information on the fluorescence signal of the fluorescence emitted from the analyte with respect to the modulation signal, and obtaining a fluorescence relaxation time constant of the fluorescence emitted from the analyte based on the third phase difference information thus obtained.

2. The fluorescence detecting method according to claim 1, wherein each of the first and the second phase difference information is data comprising a value of a signal component that is in phase with the modulation signal and a value of a signal component that is 90 degrees out of phase with the modulation signal.

3. The fluorescence detecting method according to claim 2, wherein the third phase difference information is data obtained by subtracting the second phase difference information from the first phase difference information by component.

4. A fluorescence detecting device for detecting a fluorescence emitted from an analyte by irradiating a flowing fluid formed of a buffer solution containing the analyte with laser beam, the device comprising:

a laser light source unit for emitting toward the flow laser beam having its light intensity modulated using a modulation signal having a given frequency;

a light receiving unit for generating a fluorescence signal of a fluorescence emitted by laser beam irradiation;

a timing detector for detecting a timing at which the analyte passes a position irradiated with the laser beam; and a processing/analyzing means for collecting a first fluorescence signal of a fluorescence received by the light receiving unit at a detected timing, collecting a second fluorescence signal of the fluorescence received by the light receiving unit in the absence of the analyte at a position irradiated with the laser beam after the analyte passed a position irradiated with the laser beam, adjusting a first phase difference information on the first fluorescence signal with respect to the modulation signal by using a second phase difference information on the second fluorescence signal with respect to the modulation signal to obtain a third phase difference information on the fluorescence signal of the fluorescence emitted from the analyte, and obtaining a fluorescence relaxation time constant of the fluorescence emitted from the analyte based on the third phase difference information thus obtained.

5. The fluorescence detecting device according to claim 4, wherein each of the first and the second phase difference information is data comprising a value of a signal component that is in phase with the modulation signal and a value of a signal component that is 90 degrees out of phase with the modulation signal.

6. The fluorescence detecting device according to claim 5, wherein the processing/analyzing means obtains the third phase difference information by subtracting the second phase difference information from the first phase difference information by component.

* * * * *